United States Patent [19]

Kleist

[11] 4,395,346

[45] Jul. 26, 1983

[54] METHOD FOR CLEANING CONTACT LENSES

[75] Inventor: Frederick D. Kleist, Laguna Hills, Calif.

[73] Assignee: Allergan Pharmaceuticals, Inc., Irvine, Calif.

[21] Appl. No.: 322,616

[22] Filed: Nov. 18, 1981

Related U.S. Application Data

[63] Continuation-in-part of Ser. No. 176,077, Aug. 7, 1980, abandoned, which is a continuation-in-part of Ser. No. 3,294, Jan. 15, 1979, abandoned.

[51] Int. Cl.$^3$ ........................... C11D 3/06; C11D 7/16
[52] U.S. Cl. ..................................... 252/135; 134/42;
  252/80; 252/86; 252/106; 252/173; 252/175;
  252/181; 252/DIG. 12; 252/DIG. 14
[58] Field of Search .............. 252/106, 135, 142, 175,
  252/80, DIG. 14, DIG. 11, 86, 181, 173;
  134/42; 424/78

[56] References Cited

U.S. PATENT DOCUMENTS

| | | | |
|---|---|---|---|
| 2,291,085 | 7/1942 | Lehmkuhl et al. | 252/142 X |
| 2,547,653 | 4/1951 | Minnis | 424/128 |
| 3,130,152 | 4/1964 | Fuchs | 252/175 X |
| 3,888,782 | 6/1975 | Boghosian et al. | 252/106 |
| 4,046,706 | 9/1977 | Krezanoski | 252/106 |
| 4,108,790 | 8/1978 | Foroulis | 252/175 |

*Primary Examiner*—P. E. Willis, Jr.
*Attorney, Agent, or Firm*—Stuart R. Suter; Richard D. Foggio; Alan D. Lourie

[57] ABSTRACT

A method and composition for the treatment of contact lenses, and especially soft contact lenses such as silicone and hydrophilic plastic contact lenses to remove inorganic deposits. The method consists of treating a contact lens with an aqueous solution containing an effective amount of a sequestering agent, such as a polymetaphosphate, gluconic acid or salts thereof. A preferred polymetaphosphate is sodium hexametaphosphate.

12 Claims, No Drawings

METHOD FOR CLEANING CONTACT LENSES

This application is a continuation-in-part of U.S. Ser. No. 176,077, filed Aug. 7, 1980, now abandoned, which is a continuation-in-part of U.S. Ser. No. 033,294, filed Jan. 15, 1979, now abandoned.

BACKGROUND OF THE INVENTION

1. Field of the Invention

The invention relates generally to a method and composition for the treatment of contact lenses. More particularly the invention relates to a method for the treatment of soft contact lenses to remove inorganic deposits on the lenses.

2. Background of the Prior Art

Soft contact lenses may be divided into two broad categories, namely hydrophilic and hydrophobic lenses. Hydrophobic contact lenses are usually based on elastic and flexible silicon rubber (polysiloxane), and are generally made from cross-linking dimethyl polysiloxane. Hydrophilic soft contact lenses are hydrated gel lenses which can be prepared by copolymerizing hydrophilic organic monomers containing an olefinic double bond with a small amount of a cross-linking agent which usually contains two polymerizable olefinic double bonds.

A typical preparation of a silicone contact len is disclosed in U.S. Pat. No. 3,228,741, which is hereby incorporated by reference and comprises forming a mixture of a suitable polymerization catalyst, up to 40% of a silica filler, and the silicone polymer. Said mixture is then molded and cured by heating to cross-link the polysiloxane and to produce a finished clear lens. Increased consumer acceptance of flexible silicone rubber lenses has created a need for a cleaning solution which can be used effectively with such lenses.

Hydrophilic soft contact lenses are usually based on polyhydroxylated alkyl methacrylates and contain a polyhydroxylated alkyl methacrylate, such as polyhydroxyethyl methacrylate (HEMA), cross-linked with, for example, an hydroxyethyl dimethacrylate.

One of the problems connected with these types of lenses is the formation, over a period of time, of insoluble inorganic deposits on the lenses. These deposits are thought to be primarily calcium based, e.g., calcium phosphate and calcium carbonate, but may also contain other inorganic materials and associated organic materials, e.g., protein. The presence of these insoluble inorganic deposits is a common cause of lens intolerance and decreased visual acuity.

U.S. Pat. No. 3,908,680 to Krezanoski discloses a soft contact lens cleaning system involving the cleaning of soft contact lenses by successive immersion in two aqueous solutions, with each solution containing a bleaching agent and preferably a chelating agent. The chelating agents are described by Krezanoski as water softening agents used to tie up divalent and trivalent cations, such as calcium, iron, mercury ions and the like, present in water, thereby preventing undesirable precipitates from forming and ultimately fogging the surface of the lenses.

U.S. Pat. No. 2,547,653 to Minnis, et al, discloses an aqueous solution useful in increasing the comfort of conventional hard contact lenses. The solution contains a small amount, e.g. 2–500 parts per million of a condensed phosphate such as sodium hexametaphosphate.

SUMMARY OF THE INVENTION

I have now discovered a method and composition for the treatment of contact lenses, and especially soft lenses including silicone contact lenses, hydrophilic plastic contact lenses and CAB and other semi-soft contact lenses, to remove inorganic deposits on the lenses.

The method comprises contacting a contact lens, preferably at elevated temperatures, with an aqueous solution containing an effective amount of a sequestering agent selected from the group consisting of a polymetaphosphate, gluconic acid and salts thereof for a period of time sufficient to remove existing inorganic deposits.

The composition includes an aqueous solution, such as a preserved saline solution, containing from about 0.01 to about 20% by weight of a sequestering agent selected from the group consisting of a polymetaphosphate, gluconic acid and salts thereof. The composition may additionally contain an agent for sterilizing the lenses and/or a buffer. However, no additional cleaning agents are necessary to remove inorganic deposits which may be associated with a lens.

DETAILED DESCRIPTION OF THE INVENTION

The sequestering agents which may be used in the invention are typically calcium sequestering agents such as, for example, polymetaphosphates, gluconic acid and salts thereof. Suitable polymetaphosphates include sodium polymetaphosphates such as sodium trimetaphosphate, sodium tetrametaphosphate and sodium hexametaphosphate; preferably sodium hexametaphosphate. Salts of gluconic acid which may be used include common inorganic salts such as the sodium, potassium and calcium salts as well as other salts such as, for example, calcium borogluconate. The preferred sequestering agent is sodium hexametaphosphate. All of the aforementioned compounds are well known in the art, are commercially available, and have been used heretofore for industrial processes such as, for example, leather tanning, dying, laundry and textile processing, water softening, metal plating, mordanting fabrics and as photographic processing aids. Therefore, it was surprising to discover that periodic treatment of contact lenses with aqueous solutions of these compounds safely removes inorganic deposits on the lenses without harming the lens or the eye of the user of the lens.

The amount of sequestering agent which may be used in the present invention ranges between about 0.01 and about 20% and preferably about 0.05 to about 2% by weight.

The sequestering agents may be manufactured in a number of convenient forms for use in the treatment described herein. For example, the sequestering agent could be delivered in the form of a dry, unit dosage form such as a tablet which would be dissolved in water prior to use. The sequestering agent could also form a part of a buffered or unbuffered, preserved or unpreserved, sterile, isotonic saline solution used to store the lenses. These saline solutions are well-known in the art with many being commercially available. The sequestering agents described herein may also be incorporated into cold disinfecting systems containing lens preservatives and disinfectants.

The composition is preferably used in the method at elevated temperatures between about 40° C. and about 100° C. The preferred method is to use the composition in conjunction with the conventional heat treatments used to disinfect soft lenses. These heat treatments involve daily heating of the lenses for short periods, e.g., about 15-30 minutes at a temperature of about 80° C. to about 100° C., to disinfect the lenses.

The present invention may be further described and illustrated with reference to the following examples. It is to be understood, however, that the following examples are for the purpose of illustration and the invention is not to be regarded as limited to any of the specific compounds or formulations or conditions recited therein. Unless otherwise stated, percents are by weight.

EXAMPLE I

A hydrophilic contact lens (Polymacon) which had been worn for approximately two (2) years was examined and found to have a heavy visible film deposit. The lens was cleaned with an enzymatic cleaner for 24 hours with little effect. The lens was then heated to 80° C. for 15 minutes for two (2) cycles in a 20% solution of sodium hexametaphosphate in water. The lens still retained some of the film-like material, but after one further treatment with the enzymatic cleaner, the lens was found to be free of film. This indicates that the deposit consisted of both inorganic and protein materials since the enzymatic cleaner rapidly (usually within four hours) and completely removes protein films from hydrophilic lenses.

EXAMPLE II

A hydrophilic human worn lens with an inorganic film was cleaned with an enzymatic contact lens cleaner for 24 hours. A heavy visible film remained on the lens. The lens was cut in half and one-half was heated to 80° C. for 20 minutes for four cycles in an aqueous solution containing 0.2% sodium hexametaphosphate, 0.1% boric acid, 0.01% disodium edetate, 0.85% sodium chloride preserved with 0.001% thimerosal at pH 7.4. Following another three hour treatment with the enzyme cleaner solution, the lens was free of visible deposits. The other half of the lens received only the enzyme cleaner treatment. At the end of this treatment, the lens still retained its heavy inorganic film.

EXAMPLE III

A hydrophilic human worn lens with an inorganic film was cleaned for four hours with the enzyme cleaner. No change in the film was noted. It was then alternately heated to 80° C. for 20 minutes in an aqueous solution containing 0.2% sodium gluconate, 0.1% boric acid, 0.01% disodium edetate, 0.85% sodium chloride preserved with 0.001% thimerosal at pH 7.4 and cleaned for several hours with the enzyme cleaner until three of these cycles had been completed.

Microscopic examination of the same area of the lens at each step showed almost complete removal of the heavy inorganic deposit after the three cycles. No visible deposits remained.

EXAMPLE IV

Hydrophilic contact lenses were soaked in a 1% aqueous solution of calcium chloride for 30 minutes and then placed in test solutions for 23.5 hours. This was repeated for 80 cycles. Test Solution 1 was an aqueous solution containing 0.2% polysorbate 80, 1.92% propylene glycol, 0.033% alkyl triethanol ammonium chloride, 0.05% sodium bicarbonate, 0.002% sodium chloride, 0.0023% thimerosal, and Test Solution 2 contained the same ingredients plus 0.05% sodium hexametaphosphate.

Examination of the test lenses after 80 cycles revealed calcium carbonate deposits on the lenses treated with Test Solution 1. There were no deposits of calcium carbonate on lenses treated with Test Solution 2 containing the sodium hexametaphosphate.

EXAMPLE V

In a six month controlled clinical study evaluating the safety and effiacy of the composition described in Example II, 484 patients used the composition routinely in a conventional heat disinfection regimen with their soft hydrophilic contact lenses. A control group used the same protocol except the test composition did not contain sodium hexametaphosphate. At the end of the six month study, 16% of the control group lenses contained significant inorganic deposits while none of the test group lenses contained inorganic deposits. (Four lenses in the test group contained some deposits which were easily removed by use of the test composition.)

EXAMPLE VI

The following compositions were made and found useful in removing inorganic deposits from contact lenses.

(a) An aqueous composition comprising 0.1% sorbic acid, 0.5% boric acid, 0.6% NaCl and 0.2% sodium hexametaphosphate at a pH of 6.2.

(b) Tablets weighing 148 mg were prepared containing the following ingredients: 20 mg tartaric acid, 30 mg sodium carbonate, 20 mg boric acid, 20 mg sodium hexametaphosphate, 60 mg EDTA and 48 mg NaCl.

(c) Tablets weighing 164 mg were prepared containing the following ingredients: 25 mg tartaric acid, 25 mg sodium carbonate, 20 mg boric acid, 20 mg sodium hexametaphosphate, 10 mg EDTA, 49 mg NaCl and 10 mg sorbic acid.

I claim:

1. A method for the treatment of contact lenses to remove inorganic deposits on the lenses comprising contacting a contact lens having inorganic deposits with an aqueous solution containing an amount effective for removing inorganic deposits of a sequestering agent selected from the group consisting of hexametaphosphate, gluconic acid and salts thereof for a period of time sufficient to remove inorganic deposits.

2. The method of claim 1 wherein the contact lens is selected from the group consisting of a silicone contact lens and a hydrophilic soft contact lens.

3. The method of claim 1 wherein an effective amount of sequestering agent ranges between about 0.01 and about 20% by weight.

4. The method of claim 1 wherein an effective amount of sequestering agent ranges between about 0.05 to about 2% by weight.

5. The method of claim 1 wherein the aqueous solution is a preserved isotonic saline solution.

6. The method of claim 1 wherein the sequestering agent is sodium hexametaphosphate.

7. The method of claim 1 wherein the sequestering agent is a salt of gluconic acid selected from the group consisting of sodium, potassium and calcium.

8. The method of claim 1 wherein the sequestering agent is calcium borogluconate or sodium gluconate.

9. The method of claim 1 wherein the contact lens is treated at temperatures between about 40° C. and 100° C.

10. A method of claim 1 wherein the contact lens is a silicone contact lens or a hydrophilic soft contact lens; the aqueous solution is selected from the group consisting of a sterile isotonic saline solution; a sterile buffered isotonic saline solution, a sterile preserved isotonic saline solution, and a sterile buffered preserved isotonic saline solution; the sequestering agent is sodium hexametaphosphate in an amount of 0.05 to 2% by weight; and the lens is treated at a temperature between about 40° C. and about 100° C.

11. A method for the treatment of soft contact lenses to remove calcium deposits on the lenses comprising preparing an aqueous solution by combining with water, a solid, unit dosage form of a composition consisting essentially of a sequestering agent selected from the group consisting of hexametaphosphate, gluconic acid and salts thereof and contacting a contact lens having inorganic deposits with the resulting aqueous solution at temperatures between about 40° C. and about 100° C. for a period of time sufficient to remove the calcium deposits on the lens.

12. A method for removing calcium deposits from silicone and hydrophilic soft contact lenses having calcium deposits comprising contacting a silicone or hydrophilic soft contact lens having calcium deposits at a temperature between about 40° C. and about 100° C. with a composition consisting essentially of from about 0.05 to about 2% by weight of sodium hexametaphosphate in an aqueous, preserved saline solution.

* * * * *